US007905660B2

(12) United States Patent
Sukovic et al.

(10) Patent No.: US 7,905,660 B2
(45) Date of Patent: *Mar. 15, 2011

(54) SELF-SHIELDED CT SCANNER

(75) Inventors: Predrag Sukovic, Birmingham, MI (US); Neal Clinthorne, Ann Arbor, MI (US); Miodrag Rakic, Redondo Beach, CA (US); James A. Bertolina, Portage, MI (US); Joseph Webster Stayman, Ann Arbor, MI (US)

(73) Assignee: Xoran Technologies, Inc., Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/551,723

(22) Filed: Sep. 1, 2009

(65) Prior Publication Data

US 2010/0014632 A1    Jan. 21, 2010

Related U.S. Application Data

(63) Continuation of application No. 11/674,748, filed on Feb. 14, 2007, now Pat. No. 7,593,503.

(60) Provisional application No. 60/773,232, filed on Feb. 14, 2006.

(51) Int. Cl.
*H01J 35/16* (2006.01)

(52) U.S. Cl. ............................................. 378/203

(58) Field of Classification Search ................ 378/4, 19, 378/68, 145, 102, 203; 250/515.1
See application file for complete search history.

(56) References Cited

U.S. PATENT DOCUMENTS

| 4,965,456 | A | 10/1990 | Huettenrauch et al. |
| 4,977,585 | A | 12/1990 | Boyd |
| 5,327,474 | A | 7/1994 | Inoue et al. |
| 5,499,281 | A | 3/1996 | Weedon et al. |
| 5,937,028 | A | 8/1999 | Tybinkowski et al. |
| 6,014,420 | A | 1/2000 | Ooi |
| 6,031,888 | A | 2/2000 | Ivan et al. |
| 6,304,626 | B1 | 10/2001 | Adachi et al. |
| 6,325,538 | B1 | 12/2001 | Heesch |
| 6,364,526 | B2 | 4/2002 | Ivan et al. |
| 6,530,874 | B2 | 3/2003 | Uematsu et al. |

(Continued)

FOREIGN PATENT DOCUMENTS

WO    03/073939    9/2003

(Continued)

OTHER PUBLICATIONS

International Search Report for PCT Application No. PCT/US2007/003890, Aug. 2, 2007.

*Primary Examiner* — Irakli Kiknadze
(74) *Attorney, Agent, or Firm* — Carlson, Gaskey & Olds, P.C.

(57) ABSTRACT

A CT scanner includes a pair of shields to protect an operator from x-rays from the CT scanner. The CT scanner has a gantry that provides structural support and housing for the components including an x-ray source and a detector arranged on the gantry to face one another. Lead shields are located on opposing sides of the x-ray source and extend between the x-ray source and the detector. The CT scanner further includes a computer located on an opposing side of the gantry from the x-ray source and the detector. The lead shields rotate with the gantry and prevent the x-ray from reaching the operator while the CT scanner is in operation.

24 Claims, 5 Drawing Sheets

U.S. PATENT DOCUMENTS

| | | |
|---|---|---|
| 6,554,472 B1 | 4/2003 | Dietz et al. |
| 6,661,865 B1 | 12/2003 | Popilock |
| 6,808,308 B2 | 10/2004 | Thompson |
| 7,082,185 B2 | 7/2006 | Freifeld et al. |
| 7,188,998 B2 | 3/2007 | Gregerson et al. |
| 7,409,039 B2 | 8/2008 | Banchieri et al. |
| 2003/0235266 A1 | 12/2003 | Gregerson et al. |
| 2004/0161076 A1 | 8/2004 | Goldstein |
| 2004/0258210 A1 | 12/2004 | Ritter |
| 2005/0111627 A1 | 5/2005 | Leppert |
| 2005/0135560 A1 | 6/2005 | Dafni et al. |
| 2005/0185765 A1 | 8/2005 | Chin et al. |
| 2005/0213712 A1 | 9/2005 | Cadwalader et al. |
| 2006/0182227 A1 | 8/2006 | Bernhardt |

FOREIGN PATENT DOCUMENTS

| | | |
|---|---|---|
| WO | 2005/058164 | 6/2005 |

SELF-SHIELDED CT SCANNER

REFERENCE TO RELATED APPLICATIONS

This application is a continuation of U.S. application Ser. No. 11/674,748, filed Feb. 14, 2007, now U.S. Pat. No. 7,593,503 which claims priority to U.S. Provisional Application Ser. No. 60/773,232, Feb. 14, 2006.

STATEMENT REGARDING FEDERALLY SPONSORED RESEARCH OR DEVELOPMENT

This invention was made with government support under grant number R44CA107895, awarded by the National Institute of Health (NIH). The government has certain rights in the invention.

BACKGROUND OF THE INVENTION

The present invention relates generally to computer tomography (CT) scanners and more particularly to a compact CT scanner which provides shielding of the operator from the x-rays.

Generally, CT scanners are large enough to scan a patient's entire body. An x-ray source is mounted on a movable ring, which also includes an array of x-ray detectors opposite the x-ray source. The patient lies on a platform that moves through the ring. The ring is rotated so the x-ray source and detectors revolve around the patient taking a series of x-rays, while the patient is moved through the ring on the platform. These scanners are very large because they are capable of scanning an entire body and must include a platform movable through the x-ray source and detectors. An entire room is often dedicated to such a scanner and its associated equipment. To protect the operator from the x-rays the rooms are often lined with leaded material while the operator controls the machine from a computer located outside of the room.

Recently, more compact versions of CT scanners have been provided for scanning a desired portion of a patient's body rather then scanning the entire body. Unfortunately, the operator of the system must still be protected from the x-rays emitting from the CT scanner. Therefore, rooms must still be lined with leaded material, which is expensive.

A CT scanner which protects an operator from the x-rays while providing less expensive and more compact shielding is desirable.

SUMMARY OF THE INVENTION

An example CT scanner according to this invention includes a pair of shields to protect an operator from x-rays of the CT scanner.

The CT scanner includes a gantry that provides structural support and housing for the components including an x-ray source and a detector arranged on the gantry to face one another. Lead shields are located on opposing sides of the x-ray source and extend between the x-ray source and the detector. The CT scanner further includes a computer to control the CT scanner. The computer is located on an opposing side of the gantry from the x-ray source and the detector and faces away from the gantry such that the operator is facing the patient while using the computer.

In operation, the part of the body to be scanned is positioned between the x-ray source and detector. A table for supporting the part of the body to be scanned is small enough to fit between the x-ray source and detector. The lead shields rotate with the gantry and prevent the x-ray from reaching the operator while the CT scanner is in operation. By limiting the area reached by the x-ray the exposure of the operator is limited to an acceptable amount allowing the operator to safely be in the same room as CT scanner when using the computer.

Accordingly, the lead shields of this invention provide sufficient shielding to protect the operator and the room is not required to be lined with lead.

These and other features of the present invention can be best understood from the following specification and drawings, the following of which is a brief description.

DETAILED DESCRIPTION OF THE PREFERRED EMBODIMENT

Figure 1:
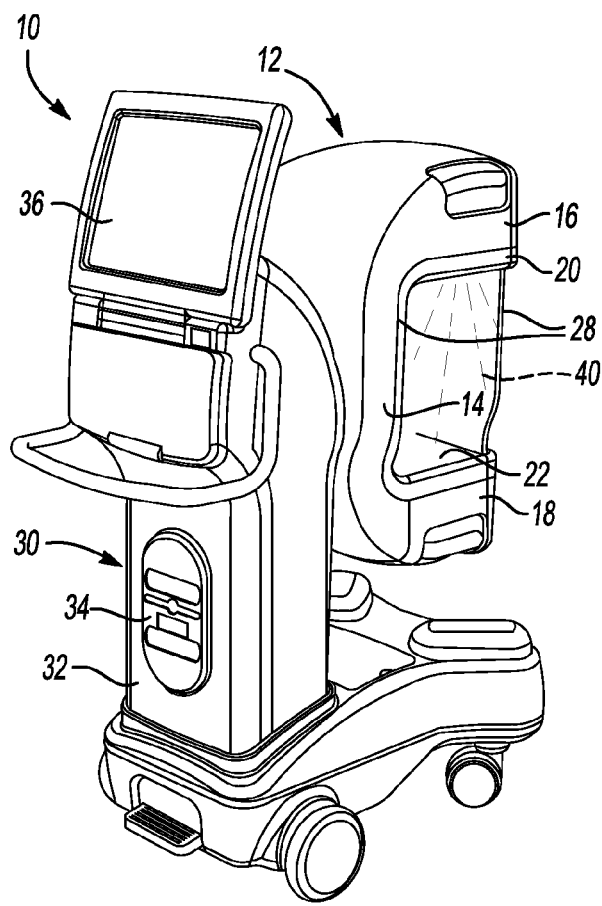
FIG. 1 is a rear perspective view of a self-shielding CT scanner of the present invention.
Figure 2:
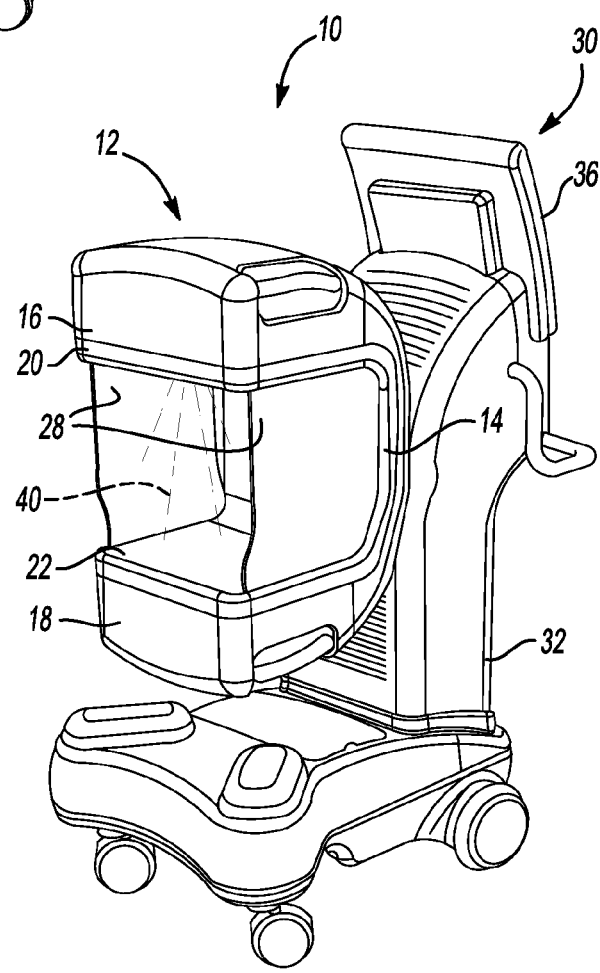
FIG. 2 is a front perspective view of a self-shielding CT scanner of the present invention.
Figure 3:
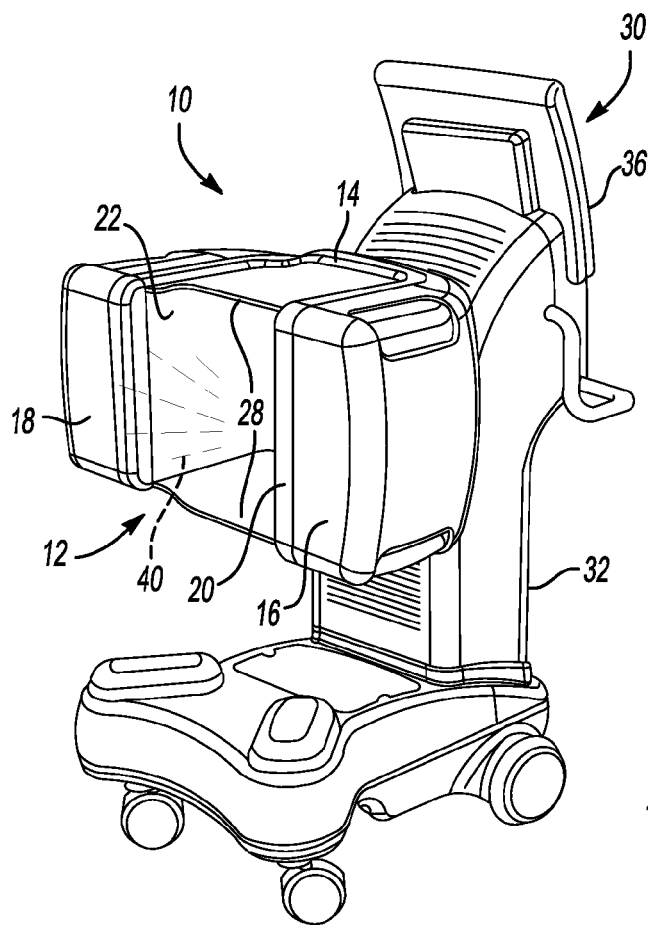
FIG. 3 is a front perspective view of a self-shielding CT scanner of the present invention.
Figure 4:
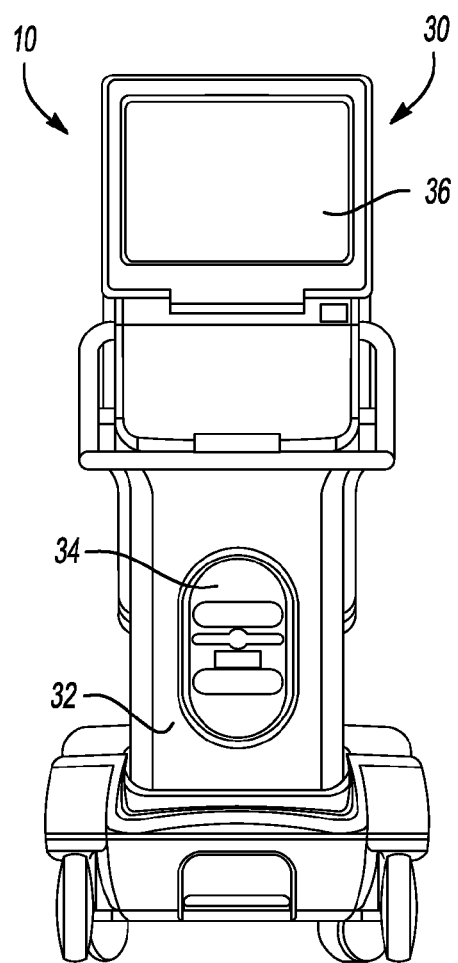
FIG. 4 is a rear view of a self-shielding CT scanner of the present invention.
Figure 5:
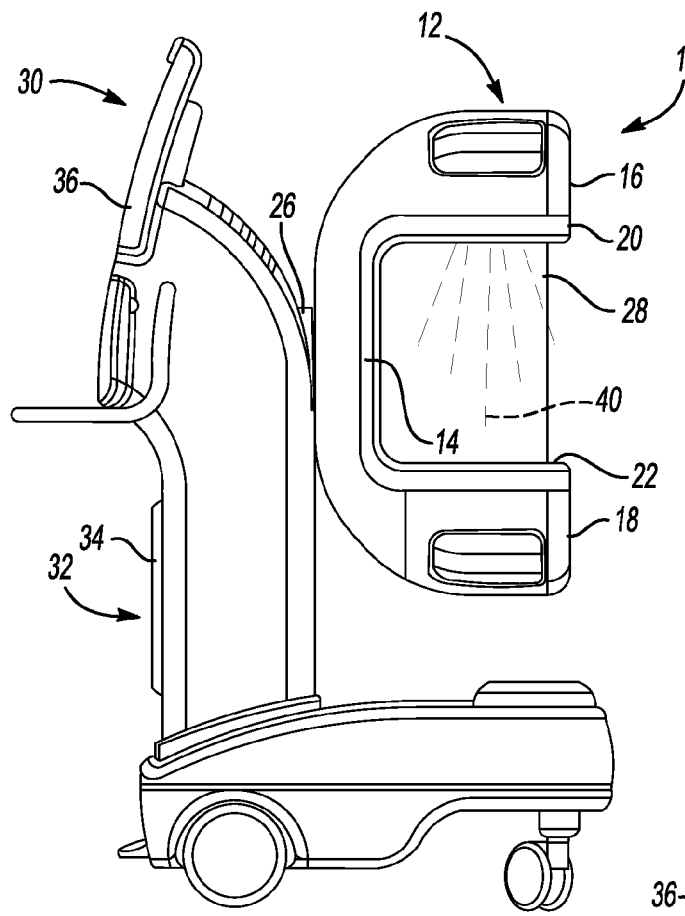
FIG. 5 is a side view of a self-shielding CT scanner of the present invention.
Figure 6:
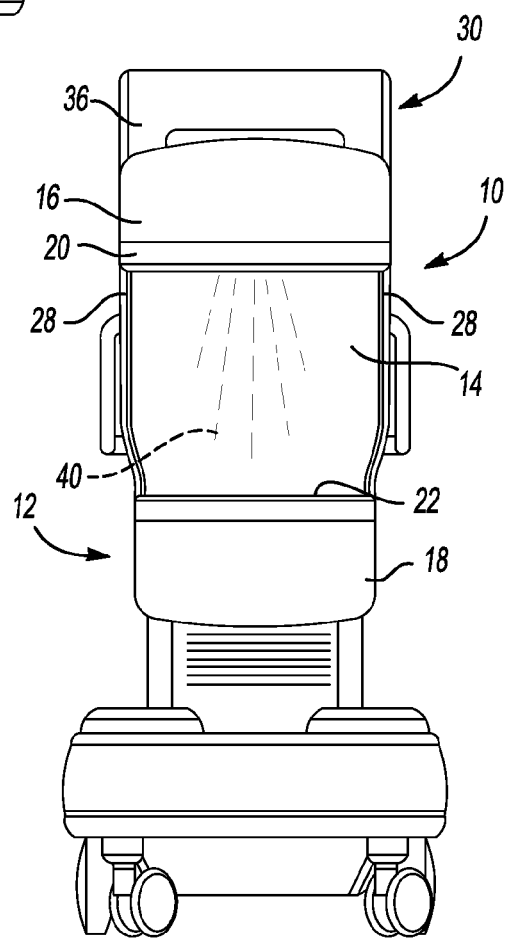
FIG. 6 is a front view of a self-shielding CT scanner of the present invention.
Figure 7:
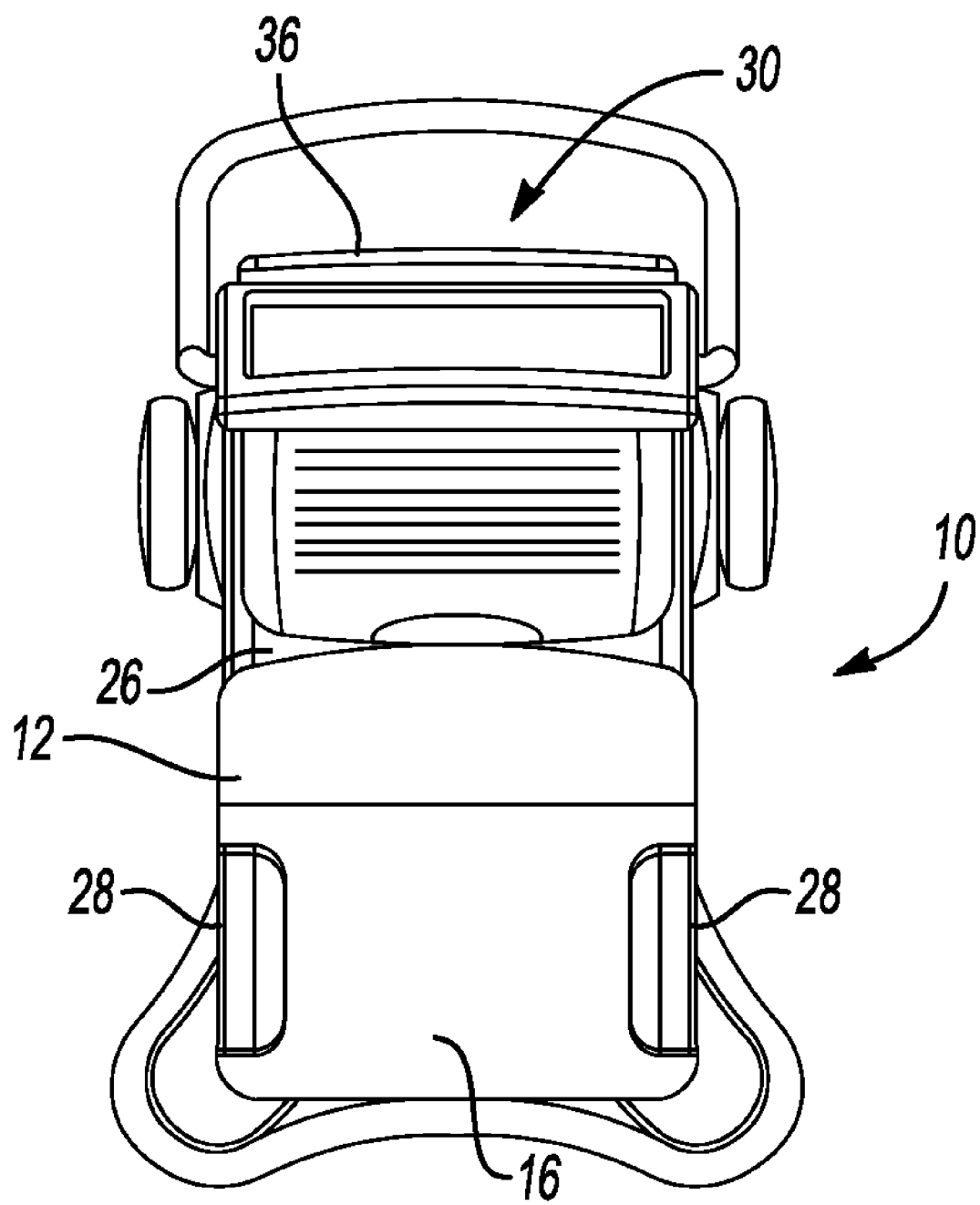
FIG. 7 is a top view of a self-shielding CT scanner of the present invention.
Figure 8:
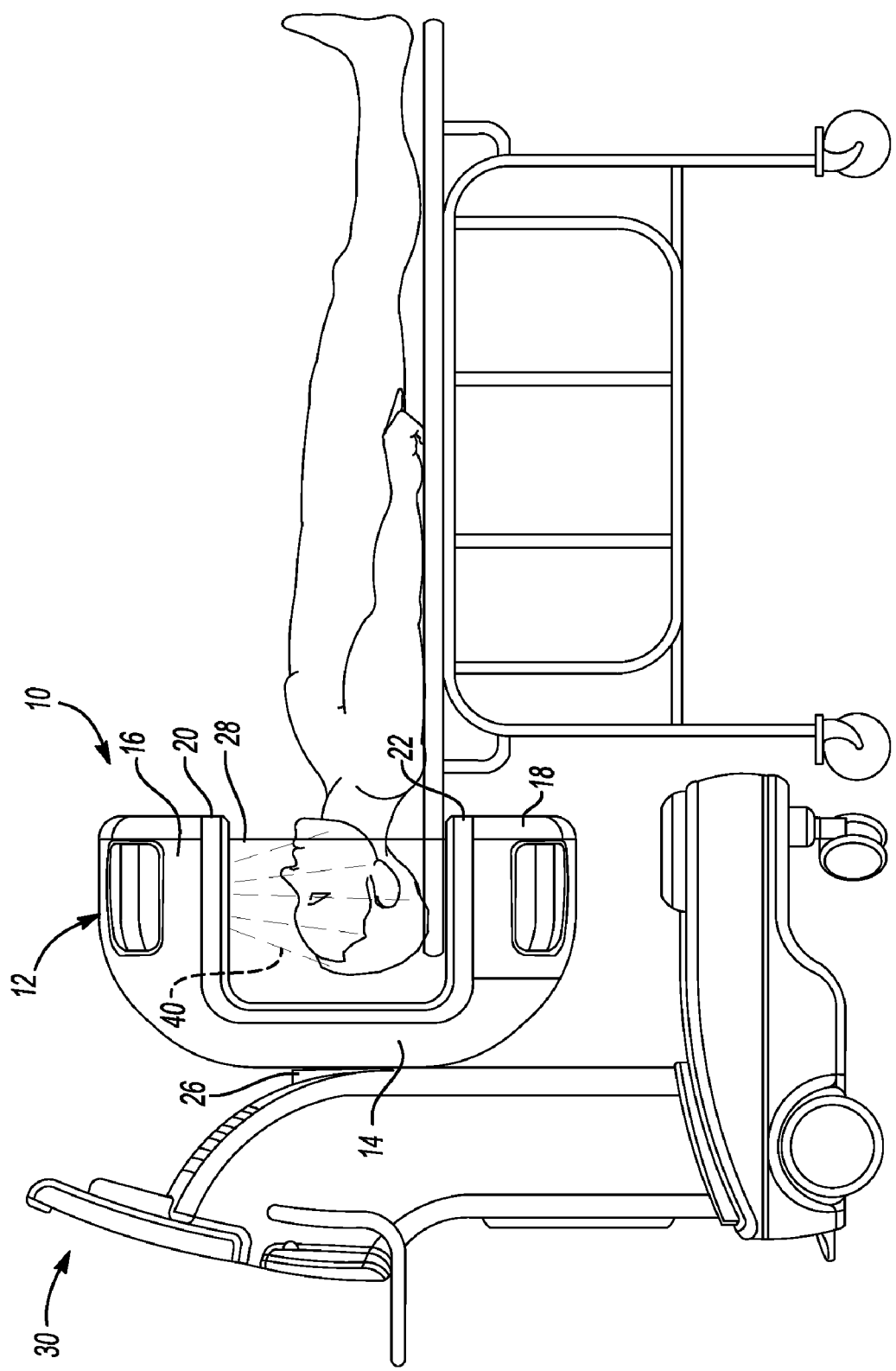
FIG. 8 is a side view of a self-shielding CT scanner of the present invention.

FIGS. 1 thru 8 illustrate a CT scanner 10 according to the present invention wherein all of the components are contained in a gantry 12. The gantry 12 provides the structural support and housing for the components. The gantry 12 comprises a cross-bar section 14 from which a first arm 16 and a second arm 18 extend perpendicularly from either end, forming a c-shaped assembly.

The first arm 16 houses the x-ray source 20, which in this embodiment is a cone-beam x-ray source 20. The second arm 18 houses a complementary detector 22. The cross-bar section 14 of the gantry 12 houses a motor for rotating the gantry 12 relative to a mounting plate 26. Lead shields 28 are located on opposing sides of the x-ray source 20. The shields 28 extend between the x-ray source 20 and the detector 22. The shields 28 are preferably leaded glass to prevent the patient from feeling closed in during use. The shields 28 may also be leaded plexiglass or some other polymer or other material that does not pass x-rays, but does permit light to pass through. The shields 28 are generally rectangular in shape to enclose the sides of the c-shaped assembly formed by the x-ray source 20, detector 22 and gantry 12.

The CT scanner 10 further includes an on-board computer 30 including a microprocessor or CPU 32, memory 34, a monitor 36 and other hardware and software for performing the functions described herein. The computer 30 controls the rotation of the CT scanner 10, the location and operation of the x-ray source 20 and x-ray detector 22 and collects the data from the detector 22 and stores it for later collection, such as in memory 34. The computer 30 is located on an opposing side of the gantry 12 from the x-ray source 20 and the detector 22. The monitor 36 faces away from the gantry 12 such that the operator is facing the patient while using the computer 30.

In operation, the part of the body to be scanned is positioned between the first arm 16 and the second arm 18 of the gantry 12. A table, or support, 38 (shown in FIG. 8) for supporting the part of the body to be scanned is small enough to fit between the first arm 16 and second arm 18, as well. The table 38 supports the body part to be scanned in order to minimize movement of the patient during the scanning while not interfering with rotation of the gantry 12.

The computer 30 powers on the x-ray source 20. The x-ray source 20 generates a cone-beam x-ray 40 that is directed toward the detector 22. The CPU 32 then controls the motor to perform one complete revolution of the gantry 12, during which time the computer 30 collects multiple images from the detector 22. The images taken by detector 22 are stored in memory 34. Because only a portion of the body is being scanned and the CT scanner 10 gathers more information in each image with the cone-beam x-ray source 20, only a single revolution or less is usually required. The shields 28 prevent the x-ray 40 from reaching the operator while the CT scanner 10 is in operation. The lead shields 28 rotate with the gantry 12. As shown, the x-ray 40 is prevented from extending past the side of the c-shaped assembly. By limiting the area of the x-ray 40 the exposure of the operator to the x-ray is limited to an acceptable amount allowing the operator to safely be in the same room as CT scanner 10 when using the computer 30. Because the shields 28 provide sufficient shielding to protect the operator the room is not required to be lined with lead. As demonstrated above, the CT scanner 10 of the present invention is compact, self-shielded and lower cost than known CT scanners.

Although a preferred embodiment of this invention has been disclosed, a worker of ordinary skill in this art would recognize that certain modifications would come within the scope of this invention. For that reason, the following claims should be studied to determine the true scope and content of this invention.

What is claimed is:

1. A computed tomography scanner comprising:
   a rotatable gantry having opposing sides that each define an opening, wherein the gantry is rotatable about an axis of rotation;
   an x-ray source mounted to the gantry;
   an x-ray detector mounted to the gantry opposite the x-ray source; and
   a shield disposed on each of the opposing sides of the gantry and extending from the x-ray source to the x-ray detector, wherein the shields are fixed relative to the gantry and prevent x-rays from passing through, and each of the shields entirely close one of the openings, preventing the passage of an object through the openings.

2. The computed tomography scanner as recited in claim 1, further including a computer and a monitor for the computer that is located outside the gantry, wherein x-rays from the x-ray source are directed away from the computer by the shields.

3. The computed tomography scanner as recited in claim 1, wherein the shields are substantially rectangular.

4. The computed tomography scanner as recited in claim 1, wherein the shields comprise leaded glass.

5. The computer tomography scanner as recited in claim 1, wherein the shields are non-flexible.

6. The computer tomography scanner as recited in claim 1, wherein the shields are each formed of a single piece of material.

7. The computed tomography scanner as recited in claim 1, wherein the shields are substantially planar.

8. The computed tomography scanner as recited in claim 1, wherein a living creature is located in the gantry.

9. A computed tomography scanner comprising:
   a rotatable gantry having opposing sides that each define an opening, wherein the gantry is rotatable about an axis of rotation;
   an x-ray source mounted to the gantry;
   an x-ray detector mounted to the gantry opposite the x-ray source; and
   a shield disposed on each of the opposing sides of the gantry and extending from the x-ray source to the x-ray detector, wherein the shields are fixed relative to the gantry and prevent x-rays from passing through, and the shields are not encased in a housing.

10. The computed tomography scanner as recited in claim 9, further including a computer and a monitor for the computer that is located outside the gantry, wherein x-rays from the x-ray source are directed away from the computer by the shields.

11. The computed tomography scanner as recited in claim 9, wherein the shields are substantially rectangular.

12. The computed tomography scanner as recited in claim 9, wherein the shields comprise leaded glass.

13. The computer tomography scanner as recited in claim 9, wherein the shields are non-flexible.

14. The computer tomography scanner as recited in claim 9, wherein the shields are each formed of a single piece of material.

15. The computed tomography scanner as recited in claim 9, wherein the shields are substantially planar.

16. The computed tomography scanner as recited in claim 9, wherein a living creature is located in the gantry.

17. A computed tomography scanner comprising:
   a rotatable gantry having opposing sides that each define an opening, wherein the gantry is rotatable about an axis of rotation;
   an x-ray source mounted to the gantry;
   an x-ray detector mounted to the gantry opposite the x-ray source; and
   a shield disposed on each of the opposing sides of the gantry and extending from the x-ray source to the x-ray detector, wherein the shields are fixed relative to the gantry and prevent x-rays from passing through, and each of the shields are directly adjacent to an object positioned in the gantry.

18. The computed tomography scanner as recited in claim 17, further including a computer and a monitor for the computer that is located outside the gantry, wherein x-rays from the x-ray source are directed away from the computer by the shields.

19. The computed tomography scanner as recited in claim 17, wherein the shields are substantially rectangular.

20. The computed tomography scanner as recited in claim 17, wherein the shields comprise leaded glass.

21. The computer tomography scanner as recited in claim 17, wherein the shields are non-flexible.

22. The computer tomography scanner as recited in claim 17, wherein the shields are each formed of a single piece of material.

23. The computed tomography scanner as recited in claim 17, wherein the shields are substantially planar.

24. The computed tomography scanner as recited in claim 17, wherein the object is a living creature.

* * * * *